United States Patent [19]

Tanaka et al.

[11] 4,049,723

[45] Sept. 20, 1977

[54] METHOD FOR SEPARATION AND RECOVERING HYDROQUINONE

[75] Inventors: Seiichi Tanaka; Kazuhiro Watari; Hideki Hayashi, all of Ohtake, Japan

[73] Assignee: Mitsui Petrochemical Industries, Ltd., Tokyo, Japan

[21] Appl. No.: 614,156

[22] Filed: Sept. 17, 1975

[30] Foreign Application Priority Data

Sept. 20, 1974 Japan .................................. 49-107665

[51] Int. Cl.$^2$ ............................................. C07C 39/08
[52] U.S. Cl. ................................ 260/621 A; 260/625; 203/44; 203/45; 203/46; 260/621 C
[58] Field of Search ............ 260/621 A, 621 C, 627 R, 260/621 B, 625, 624 A; 203/44, 45, 46

[56] References Cited

U.S. PATENT DOCUMENTS

| | | | |
|---|---|---|---|
| 3,365,375 | 1/1968 | Nixon | 260/621 C |
| 3,376,352 | 4/1968 | Domenicali | 260/621 C |

*Primary Examiner*—James O. Thomas, Jr.
*Assistant Examiner*—W. B. Lone
*Attorney, Agent, or Firm*—Wenderoth, Lind & Ponack

[57] ABSTRACT

A method for separating and recovering hydroquinone which comprises distilling a by-product-containing acid-cleavage product, which is obtained by acid-cleavage of an oxidation product of para-diisopropyl benzene in a solvent, in the presence of an aromatic hydrocarbon, thereby removing low-boiling fractions including the solvent, bringing the resulting hydroquinone-containing distillation bottoms into contact with water, and crystallizing and separating hydroquinone; characterized in that a. the distilling off of the low-boiling fractions is effected without the addition of water and in the absence of an azeotropic amount of water and also in the presence of an aromatic hydrocarbon containing 9 to 10 carbon atoms, and b. the contacting of the distillation bottoms with water is effected under conditions which do not induce crystallization of hydroquinone in the distillation bottoms.

2 Claims, No Drawings

METHOD FOR SEPARATION AND RECOVERING HYDROQUINONE

This invention relates to an improved method for separating and recovering high purity hydroquinone, in high yields by an easy operation, from an acid-cleavage product containing by-products which is obtained by acid-cleavage of an oxidation product of para-diisopropyl benzene in a solvent such as a ketone.

It is known to separate and recover hydroquinone from an acid-cleavage product which is obtained by acid-cleavage, in a ketone solvent such as methyl isobutyl ketone and in the presence of an acid catalyst, of an oxidation product containing para-diisopropylbenzene dihydroperoxide (DHP) prepared by oxidation of para-diisopropyl benzene (DIPB) with molecular oxygen. As is well known, in the above-mentioned oxidation reaction to produce DHP from DIPB, para-diisopropylbenzene monohydroperoxide (MHP) is formed from DIPB, and this intermediate is further oxidized to DHP. Even when the operation is performed so as to effect the oxidation reaction sufficiently in order to increase the amount of DHP, decomposition reactions of MHP and DHP take place in competition with the oxidation reaction, and the amount of DHP obtained is naturally restricted. It is a common practice therefore to stop the oxidation reaction at a suitable time when the amount of useful substances derived from the starting DIPB becomes maximum. As a result, the oxidation reaction product of para-diispropyl benzene usually contains fairly large quantities of by-products such as MHP, para-2-hydroxy-2-propyl-$\alpha,\alpha$-dimethylbenzyl hydroperoxide, alcohols, olefins and tarry substances in addition to DHP as a main product.

Direct separation of DHP from such an oxidation product requires a complex and difficult operation of separating DHP from such fairly large quantities of various by-product, which leads to a low rate of recovery of DHP and poses a problem of treating the separated products. These drawbacks, therefore, render such a direct separating method economically disadvantageous. In an attempt to overcome such a disadvantage, some suggestions have heretofore been made to acid-cleave the above oxidation product containing by-products, and separate hydroquinone from the resulting acid-cleavage product. It is considerably difficult however to separate high purity hydroquinone from the acid-cleavage product advantageously in respect to both operation and yield.

As a suggestion for separating and recovering hydroquinone from the acid-cleavage product, Japanese Patent Application Publication No. 72140/73 (laid open on Sept. 29, 1973) discloses a process which comprises distilling off acetone from an acid-cleavage product obtained by acid-cleavage of an oxidation product of para-diispropyl benzene in a methyl isobutyl ketone solvent, then distilling off the methyl isobutyl ketone from the acid-cleavage product in the presence of water, especially in the presence of at least an azeotropic amount of water sufficient to distill off the methyl isobutyl ketone as an azeotrope with water, thereby to obtain crude hydroquinone in the form of an aqueous solution as distillation bottoms, extracting the aqueous phase of the bottoms with an aromatic hydrocarbon to remove impurities therein, and then crystallizing and separating hydroquinone from the aqueous phase. According to this process, a large quantity of water is present in the distillation system when distilling off low-boiling fractions including the methyl isobutyl ketone, and therefore, an emulsion tends to be formed. Once an emulsion is formed, it is extremely difficult to remove it from the aqueous phase of the bottoms. The process, therefore, requires a complex and carefully controlled operation that can avoid the formation of an emulsion. Such an operational defect makes it extremely difficult to perform the process on an industrial scale.

As another suggestion, Japanese Patent Application Publication No. 18836/74 (laid open on Feb. 19, 1974) discloses a process for purifying hydroquinone which comprises adding an azeotropic amount of water and if desired, a hydrocarbon solvent such as benzene, toluene or xylene to acetone, methyl ethyl ketone or a ketone capable of forming an azeotrope with water having crude hydroquinone dissolved therein, distilling off low-boiling fractions including the ketone solvent, treating the resulting hydroquinone-containing distillation bottoms with a hydrocarbon solvent and if desired, water, separating the aqueous phase, and then crystallizing and separating hydroquinone from the aqueous phase. Since in this process also, the distillation is performed in the presence of an azeotropic amount of added water, there is an operational difficulty in avoiding the formation of an emulsion as in the case of the first-mentioned prior suggestion.

On the other hand, in an attempt to prevent hydroquinone from being contaminated by impurities, U.S. Pat. No. 3,376,352 suggests a method in which the acid-cleavage is carried out in the presence of a ketone solvent and an aromatic hydrocarbon such as benzene, toluene or xylene. In this method, a hydroquinone-containing distillation bottoms can be obtained as suspended in the aromatic hydrocarbon without being contacted with water, and is separated by mechanical means such as filtration. According to the Examples in this patent, hydroquinone of high purity is obtained in superior yields, but the patent fails to disclose any example in which hydroquinone is separated and recovered from the acid-cleavage product containing by-products as described hereinabove. In fact, even when such a separating procedure is applied to the by-product-containing acid-cleavage product, the by-products are occluded in the hydroquinone crystals, and cannot be removed easily. When complex and disadvantageous means are employed to remove such by-products, purification losses are great, and an unreasonable reduction in yield cannot by avoided.

We made extensive investigations in an attempt to provide an improved process which can overcome the various disadvantages in the prior suggestions, and can separate and recover high purity hydroquinone in high yields by an industrially advantageous easy operation. These investigations finally led to the discovery that the various defects of the prior art can be overcome and high purity hydroquinone can be separated and recovered in high yields by an industrially advantageous easy operation by distilling an acid-cleavage product in the presence of an added aromatic hydrocarbon containing 9 to 10 carbon atoms and in the absence of an azeotropic amount of water and without adding water, the acid-cleavage product being one obtained by acid-cleavage of an oxidation product of para-diispropyl benzene in a ketone solvent, preferably methyl isobutyl ketone, thereby to remove low-boiling fractions including the ketone solvent; withdrawing the hydroquinone-containing distillation bottoms in the liquid state, namely under conditions not inducing the crystallization of hydroquinone; bringing the hydroquinone-containing distillation bottoms into contact with water under conditions not inducing the crystallization of hydroquinone; separating the aqueous phase; and crystallizing and separating hydroquinone from the aqueous phase; it being especially preferable, to bring the aqueous phase into contact with methyl isobutyl ketone to extract hydroquinone from the aqueous phase into the methyl isobutyl ketone phase, followed by crystallizing and separating the hydroquinone from the ketone phase.

Accordingly, it is an object of this invention to provide an improved method for separating and recovering high purity hydroquinone in high yields by an easy operation from an acid-cleavage product of an oxidation product of para-diisopropyl benzene obtained in a solvent.

Other objects and advantages of this invention will become apparent from the following description.

Methods for oxidizing para-diisopropyl benzene and for acid-cleaving the resulting oxidation product are well known in the art, and the acid-cleavage products used as starting materials in the present invention can be obtained by these known methods, for example, those disclosed in Japanese Patent Publications Nos. 3618/52 and 3875/72.

For example, an oxidation product of DIPB is directly cleaved in the presence of an acid-cleaving catalyst, for example, sulfuric acid, perchloric acid, phosphoric acid, p-toluenesulfonic acid, or an ion-exchange resin. Methyl isobutyl ketone is most suitable as the ketone solvent used for acid-cleavage. Aromatic hydrocarbons used in a step of distilling low-boiling fractions can be used as solvents together with the ketone solvent.

The effluent from the acid-cleaving step contains isopropyl phenol, various alcohols, tarry substances and, at times, the solvent used for acid-cleavage, in addition to acetone and hydroquinone as main products, although this differs according to the starting material and solvent used for acid-cleavage. When the effluent contains an acidic substance used as the catalyst, it is advisable to subject it to a distillation step after removing the acidic substance by, for example, neutralization.

It is especially important in the present invention that low-boiling fractions are distilled off from the acid-cleavage product in the presence of an added aromatic hydrocarbon containing 9 to 10 carbon atoms, and that the hydroquinone-containing distillation bottoms are contacted with water under conditions which do not induce the crystallization of hydroquinone, for example, under conditions which maintain hydroquinone in the liquid state, that is, while hydroquinone is dissolved in the by-products or aromatic hydrocarbon or it is melted. At this time, it is important that water should be substantially absent in the distillation bottoms although the presence of a tiny amount of water is permissible; in other words, the distillation is carried out without adding water and in the absence of an azeotropic amount of water.

When a solvent having a boiling point between the boiling point of the aromatic hydrocarbon to the present in the distillation of low-boiling fractions and that of acetone is used in the acid-cleavage of the oxidation reaction product of DIPB, the aromatic hydrocarbon can be added after distilling off acetone. Otherwise, it is recommended that the aromatic hydrocarbon be present before the distillation of acetone. For example, when methyl isobutyl ketone is used in the acid-cleavage, acetone is first distilled off, and then methyl isobutyl ketone is distilled off while causing a distillable aromatic hydrocarbon having a boiling point higher than the methyl isobutyl ketone to be present in the distillation system, after which hydroquinone containing heavy by-products are withdrawn from the bottom of the still together with the aromatic hydrocarbon. Generally, the temperature of the bottom of the still should be at least 150° C. although it varies according to the types or amounts of the heavy by-products. However, if it is too high, the decomposition of tar, for example, occurs, and therefore, the bottom temperature is maintained preferably at about 150° to 190° C. The use of aromatic hydrocarbons containing 9 to 10 carbon atoms, for example, cumene or cymene, has the advantage that their separation from methyl isobutyl ketone is good, and the still bottom can easily be maintained at a temperature of at least 150° C. even in vacuum distillation.

When acetone is used as a solvent in the acid-cleaving, the aromatic hydrocarbon containing 9 to 10 carbon atoms must be caused to be present at the time of distilling off acetone. In order to maintain the still bottom temperature as mentioned above without applying pressure during distillation, it is necessary to use aromatic hydrocarbons containing 9 to 10 carbon atoms and having a high boiling point. The distillation operation becomes increasingly difficult as the number of carbon atoms of the aromatic hydrocarbon decreases. Aromatic hydrocarbons having a larger number of carbon atoms are disadvantageous in respect to heat energy at the time of recovery.

The hydroquinone-containing distillation bottoms obtained by distilling off low-boiling fractions including the solvent is brought into contact with water under conditions which do not induce the crystallization of hydroquinone, and is thus dissolved in water. Since the rate of dissolving hydroquinone is sufficiently fast, the dissolving can be performed, for example, by introducing water in an exhaust pipe at the bottom of the distillation still. When hydroquinone is first crystallized from the distillation bottoms and then contacted with water, a tarry substance adheres to the hydroquinone crystals, and reduces the efficiency of extracting the hydroquinone into water.

The suitable amount of the aromatic hydrocarbon containing 9 to 10 carbon atoms to be present at the time of distillation is preferably about 15 to 100 parts by weight per 100 parts by weight of hydroquinone, and the suitable amount of water to be used for extraction is preferably about 100 to 5,000 parts by weight per 100 parts by weight of hydroquinone.

After extraction with water, the extraction system is allowed to stand thereby to separate it into an oily phase and an aqueous phase. The aqueous phase is concentrated to crystallize hydroquinone. Hydroquinone can be recrystallized from water or acetone. Especially good results can be obtained by separating the aqueous phase after contacting the distillation bottoms with water, bringing the aqueous phase into contact with methyl isobutyl ketone thereby to extract the hydroquinone from the aqueous phase into the methyl isobutyl ketone phase, concentrating the ketone phase to crystallize hydroquinone, and recrystallizing the hydroquinone as mentioned above. This ensures an effective removal of even tiny amounts of oily impurities. In order to remove the oily impurities completely, the hydroquinone is recrystallized preferably from acetone or a mixture of water and acetone. But since acetone is liable to form an adduct with hydroquinone, it is better to recrystallize hydroquinone in a mixture of acetone and water under conditions which do not cause the formation of a hydroquinone-acetone adduct. These conditions can be attained by selecting the mixing ratio between acetone and water and the crystallizing temperature.

The following Examples and Comparative Examples illustrate the present invention in greater detail.

EXAMPLE 1 AND COMPARATIVE EXAMPLES 1 and 2

An oxidation product of DIPB was acid-cleaved in a methyl isobutyl ketone solvent in the presence of a sulfuric acid catalyst. The reaction product was neutralized with an aqueous solution of sodium hydroxide, and the aqueous phase was removed. The resulting by-product-containing acid-cleavage product had the following composition.

| | |
|---|---|
| Acetone | 15% by weight |
| Methyl isobutyl ketone | 47% by weight |
| Hydroquinone | 12% by weight |
| Isopropylphenol | 4% by weight |
| Other components, mainly by-products | 16% by weight |
| Water | 6% by weight |

The acid-cleavage product was fed into a first distillation tower, and a part of water and acetone were distilled off from the top of the first distillation tower. Cumene in an amount 0.8 time the amount of hydroquinone was added to the distillation bottoms, and the mixture was fed into a second distillation tower where methyl isobutyl ketone and the remaining water were distilled off. By maintaining the top of the second tower at 100 mmHg and 70° C. and its bottom at 170° C., a liquid effluent consisting of 23% by weight of cumene, 29% by weight of hydroquinone, 10% by weight of isopropyl phenol, and 38% of other components, mainly by-products, was withdrawn from the bottom of the tower. Water at 30° C. in an amount 4 times the amount of hydroquinone was added to the hydroquinone-containing distillation bottoms so withdrawn, and the mixture was cooled. After standing, the aqueous phase was separated, and concentrated. Hydroquinone was crystallized, and recrystallized from acetone. On the other hand, the above aqueous phase was contacted with methyl isobutyl ketone (MIBK). The methyl isobutyl ketone phase was separated, and concentrated to crystallize hydroquinone.

The hydroquinone was recrystallized from acetone.

In both cases, the purity, recovery yield, color (APHA) and oily impurity content of the purified hydroquinone were examined, and the results are shown in Table 1.

The purity was measured in accordance with JIS K8738; APHA was determined by comparing the color of 100 ml. of a solution of 5g hydroquinone in a 5% aqueous solution of acetic acid with that of a standard solution in accordance with ASTM D 1209-69; and the oily impurity content was measured by gas chromatography based on internal standards using a filled column and a nitrogen gas as a carrier.

For comparison, an acid-cleavage product was prepared in the same way as in Example 1 except that the acid-cleavage was effected in a solvent consisting of methyl isobutyl ketone and cumene in a mixing ratio of 1 : 2.5. The acid-cleavage product had the following composition.

| | |
|---|---|
| Acetone | 7% by weight |
| Methyl isobutyl ketone | 22% by weight |
| Cumene | 54% by weight |
| Hydroquinone | 6% by weight |
| Isopropyl phenol | 2% by weight |
| Other components, mainly by-products | 7% by weight |
| Water | 2% by weight |

The resulting acid-cleavage product was fed into a first distillation tower, and 32 parts of acetone and 1 part of water were distilled off from the top of the tower. Furthermore, in a second distillation tower, 100 parts of methyl isobutyl ketone and 7 parts of water were distilled off from the top of the tower and thus separated from the cumene suspension as distillation bottoms. Crude hydroquinone was separated from the cumene suspension by filtration, and dried. The cumene suspension formed three phases, an oily phase of undissolved by-products, an oily phase of cumene and undissolved by-products, and a solid phase of hydroquinone. The undissolved by-product oily phase adhered to the solid, and the resulting hydroquinone had a purity of only 91%. 25.9 parts of crude hydroquinone crystals were obtained, and the yield of 100% pure hydroquinone was 97.:% based on DHP in the by-product-containing acid-cleavage product.

The resulting hydroquinone was recrystallized from acetone in the same way as in Example 1 (Comparative Example 1). The results are also shown in Table 1.

For further comparison, 60 parts of a 0.03% aqueous solution of sodium bisulfite and 60 parts of xylene were added to 40 parts of the same acid-cleavage product as obtained in Example 1. The mixture was distilled to remove 6.4 parts of acetone, 20 parts of methyl isobutyl ketone, 1.4 parts of water and 0.3 parts of xylene. The aqueous phase of the distillation bottoms formed an emulsion together with an oily phase containing by-products. Therefore, 30 parts of xylene was further added, and on standing, the aqueous phase was centrifugally separated for 5 minutes with a centrifugal force of 2000 G. Despite this, the emulsion was not destroyed. The crude hydroquinone crystals obtained by concentrating the aqueous phase had a purity of 98.8%. The yield of 100% pure hydroquinone was 84.0% based on DHP in the by-product-containing acid-cleavage product.

The resulting hydroquinone was recrystallized from acetone in the same way as in Example 1 (Comparative Example 2). The results are shown in Table 1.

Table 1

| | Hydroquinone recrystallized from acetone | | | | Hydroquinone recrystallized from methyl isobutyl ketone and then from acetone | | | |
|---|---|---|---|---|---|---|---|---|
| Runs | Purity (%) | Oily Impurity content (ppm) | Color (APHA) | Recovery yield (%) | Purity (%) | Oily Impurity content (ppm) | Color (APHA) | Recovery yield (%) |
| Example | | | | | | | | |

Table 1-continued

| | Hydroquinone recrystallized from acetone | | | | Hydroquinone recrystallized from methyl isobutyl ketone and then from acetone | | | |
|---|---|---|---|---|---|---|---|---|
| Runs | Purity (%) | Oily Impurity content (ppm) | Color (APHA) | Recovery yield (%) | Purity (%) | Oily Impurity content (ppm) | Color (APHA) | Recovery yield (%) |
| 1 | 99.5 | 50 | 25-25 | 100 | 99.7 | 20 | 10-15 | 100 |
| Comparative Example 1 | 97.0 | 26,000 | 500 | 97.1 | — | — | — | — |
| Comparative Example 2 | 99.4 | 1,600 | 60-70 | 84.0 | — | — | — | — |

EXAMPLE 2

The same acid-cleavage product as used in Example 1 was distilled in the same way as in Example 1 except that cymene was used instead of cumene. The resulting distillation bottoms had the following composition.

| | |
|---|---|
| Cymene | 22% by weight |
| Methyl isobutyl ketone | 3% by weight |
| Hydroquinone | 28% by weight |
| Isopropylphenol | 10% by weight |
| Others | 37% by weight |

Water in an amount eight times the amount of hydroquinone was added to the distillation bottoms, and the same procedure as in Example 1 was repeated. The results are shown in Table 2.

COMPARATIVE EXAMPLE 3

The same acid-cleavage product as used in Example 1 was distilled in the same way as in Example 1 except that xylene was used instead of cumene, and acetone, methyl isobutyl ketone and water were distilled off at a still bottom temperature of 155° C. The distillation bottoms obtained had the following composition.

| | |
|---|---|
| Xylene | 22% by weight |
| Hydroquinone | 29% by weight |
| Isopropyl phenol | 10% by weight |
| Others | 39% by weight |

Water in an amount 4 times the amount of hydroquinone was added to the distillation bottoms, and the same procedure as in Example 1 was repeated. The results are shown in Table 2.

COMPARATIVE EXAMPLE 4

The same acid-cleavage product as used in Example 1 was distilled in the same way as in Example 1 except that para-diisopropyl benzene was used instead of cumene, and acetone, a part of methyl isobutyl ketone, and water were distilled off at a still bottom temperature of 180° C. The resulting distillation bottoms had the following composition.

| | |
|---|---|
| Methyl isobutyl ketone | 4% by weight |
| para-Diisopropyl benzene | 30% by weight |
| Hydroquinone | 26% by weight |
| Isopropyl phenol | 8% by weight |
| Others | 32% by weight |

Water in an amount four times the amount of hydroquinone was added to the distillation bottoms, and the same procedure as in Example 1 was repeated. The results are shown in Table 2.

Table 2

| | | Hydroquinone recrystallized from acetone | | | | Hydroquinone recrystallized from methyl isobutyl ketone and then from acetone | | | |
|---|---|---|---|---|---|---|---|---|---|
| Runs | Aromatic hydrocarbon used | Purity (%) | Oily Impurity content (ppm) | Color (APHA) | Recovery yield (%) | Purity (%) | Oily Impurity content (ppm) | Color (APHA) | Recovery yield (%) |
| Example 2 | Cymene (C$_{10}$) | 99.5 | 60 | 25-30 | 98.8 | 99.7 | 18 | 10-15 | 98.8 |
| Comparative Example 3 | Xylene (C$_8$) | 98.4 | 250 | 100 | 99.3 | 99.8 | 150 | 70 | 95.5 |
| Comparative Example 4 | p-DIPB (C$_{12}$) | 98.4 | 400 | 250 | 96.6 | 99.6 | 300 | 150-200 | 91.0 |

What we claimed is:

1. In a method for separating and recovering hydroquinone from a by-product-containing acid-cleavage product obtained by acid-cleavage of an oxidation product of para-diisopropyl benzene in method isobutyl ketone as a solvent, which comprises distilling said by-product-containing acid-cleavage product in the presence of an added aromatic hydrocarbon to remove low-boiling fractions, including the solvent, contacting the resultant hydroquinone-containing distillation bottoms with water, and crystallizing and separating hydroquinone, the improvement wherein
   a. the distillation to remove the low-boiling fractions is effected without the addition of water and in the absence of an azeotropic amount of water, and also in the presence of about 15 to 100 parts by weight of an added aromatic hydrocarbon selected from the group consisting of cumene and cymene per 100 parts by weight of the hydroquinone, b. the contact of the hydroquinone-containing distillation bottoms with water is effected under conditions such that the temperature of said bottoms is about 150 to 190° C, the water is used in an amount of about 100 to 5000 parts by weight per 100 parts by weight of the hydroquinone, and the hydroquinone in the hydroquinone-containing distillation bottoms is extracted into the water, thereby avoiding crystallization of the hydroquinone in the distillation bottoms, and, after the extraction, the mixture resulting from the extraction is separated into an aqueous phase and an oily phase, and the hydroquinone is separated from the aqueous phase.

2. The method of claim 1, wherein the hydroquinone is separated from the aqueous phase by contacting the aqueous phase with methyl isobutyl ketone to extract the hydroquinone from the aqueous phase into the methyl isobutyl ketone phase, and the hydroquinone is crystallized and separated from the methyl isobutyl ketone phase.

* * * * *